United States Patent [19]

Rothe et al.

[11] 4,223,089

[45] Sep. 16, 1980

[54] PROCESS AND DIAGNOSTIC DEVICE FOR THE DETERMINATION OF AMMONIA AND OF SUBSTRATES WHICH REACT WITH THE FORMATION OF AMMONIA

[75] Inventors: Anselm Rothe; Adolf K. Selle, both of Birkenau; Hans-Rudolf Lange, Lampertheim; Walter Rittersdorf; Wolfgang Werner, both of Mannheim, all of Fed. Rep. of Germany

[73] Assignee: Boehringer Mannheim GmbH, Mannheim, Fed. Rep. of Germany

[21] Appl. No.: 34,719

[22] Filed: Apr. 30, 1979

[30] Foreign Application Priority Data

May 17, 1978 [DE] Fed. Rep. of Germany ....... 2821469

[51] Int. Cl.² ............... G01N 31/14; G01N 33/16; G01N 21/06; G01N 31/22
[52] U.S. Cl. ............................ 435/12; 23/230 B; 23/924; 422/56; 435/805; 435/15; 435/18
[58] Field of Search ............ 23/230 B, 924; 422/56; 435/12, 805

[56] References Cited

U.S. PATENT DOCUMENTS

| 3,249,513 | 5/1966 | Babson | 435/12 |
| 3,427,225 | 2/1969 | Harvill | 435/12 |
| 3,528,780 | 9/1970 | Radawski | 422/56 X |
| 3,531,254 | 9/1970 | Okudd | 422/56 X |
| 3,607,093 | 9/1971 | Stone | 422/56 |
| 3,723,064 | 3/1973 | Liotta | 422/56 |
| 3,791,933 | 2/1974 | Moyer | 422/56 |
| 3,798,004 | 3/1974 | Zerachia | 422/56 |
| 3,809,617 | 5/1974 | Schmitt | 422/56 |
| 3,846,247 | 11/1974 | Kronish | 422/56 X |
| 3,873,269 | 3/1975 | Kraffczyk | 422/56 X |
| 3,884,641 | 5/1975 | Kraffczyk | 422/12 |
| 3,901,657 | 8/1975 | Lightfoot | 422/56 |
| 3,926,734 | 12/1975 | Gray | 435/12 |
| 4,061,468 | 12/1977 | Lange | 422/56 |
| 4,160,008 | 7/1979 | Fenocketti | 422/56 |

Primary Examiner—Sidney Marantz

[57] ABSTRACT

Diagnostic device for the determination of ammonia having a handle, an ammonia indicator layer thereon and an alkaline buffer-containing reaction layer positioned above the indicator layer a distance of 10 to 200 microns by a spacer member. The reaction layer is readily separated from the indicator layer to reveal the latter at the end of the ammonia test.

13 Claims, 1 Drawing Figure

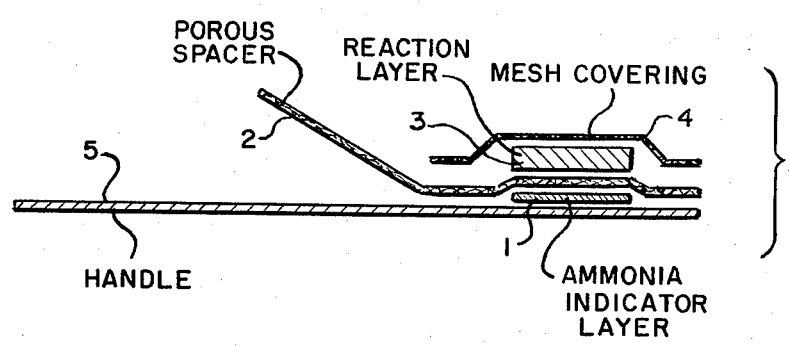

PROCESS AND DIAGNOSTIC DEVICE FOR THE DETERMINATION OF AMMONIA AND OF SUBSTRATES WHICH REACT WITH THE FORMATION OF AMMONIA

BACKGROUND

This invention relates to a process and diagnostic device for the determination of ammonia and of substrates which react with the formation of ammonia.

The determination of urea in body fluids is of great importance for the diagnosis and monitoring of diseases of the kidney. For some time now, a number of wet chemical processes have been available for this purpose which depend upon the following principles: In the case of a direct method, urea is reacted with diacetylmonoxime and the adsorption of the resulting compound is measured photometrically. Other more modern methods have, prior to the color reaction, an enzymatic step in which the urea is decomposed to ammonium carbonate by means of the enzyme urease. The ammonia is subsequently reacted, for example in the known Nessler color reaction or is converted according to berthelot's method, with phenol/hypochlorite, into a colored indophenol. The extinction of the colored reaction products formed by these reactions is finally a measure of the amount of urea initially present.

These processes are themselves of sufficient exactitude but, nevertheless, require the use of expensive photometers and trained personnel with sufficient experience in precise pipetting and in handling reagents, some of which are of limited stability and are also corrosive. Since these processes cannot be applied to whole blood, additional laboratory devices are necessary in order to obtain serum or plasma.

In emergency cases, for example in cases of uraemic coma, it is essential for the therapeutic measures which have to be taken that an accurate analytical result be available in the shortest possible time. Therefore, extensive efforts have also been made to develop methods for the determination of urea in body fluids which enable analysis results to be obtained in the shortest possible time which are of good diagnostic value.

Rapid tests in the form of test strips have recently achieved importance because of simplicity of handling and, in some cases, also the shorter reaction time, as well as the usability at the sick bed and in emergencies, and also use by untrained personnel or even by the patients themselves.

A rapid test for the determination of urea in body fluids, such as blood, serum and plasma, is described in German Pat. No. 1,240,306. In this case, urease, pH indicator, buffer and adjuvants are impregnated together onto a paper. Upon dropping a body fluid thereon, neutral-reacting urea contained therein is converted into ammonium carbonate, which has an alkaline reaction. The change in pH is indicated by a change in color of the pH indicator and the urea content of the sample can be estimated by comparison with comparative colors. In spite of certain advantages, such as ease of handling and a short reaction time, these test strips can only be used for rough estimations because of the difficulty of differentiating their reaction colors and because of the marked influence of the acid-base content of the body fluid.

The problem of dependence upon the acid-base content of body fluids is solved by strips described in German Pat. No. 1,245,619 in which an absorbent paper strip is impregnated side-by-side with three different solutions. in the case of these test strips, the urea-containing solution is first absorbed into a urease-containing test zone in which the urea reacts to give ammonium carbonate. The solution is then transferred by capillary forces to a neighboring alkaline test zone which liberates gaseous ammonia from the ammonium carbonate which passes over the gas space surrounding the test strips into a third test zone and colors a pH indicator present therein corresponding to the concentration of the urea. Transmission of the alkaline solution is prevented by means of an approximately 2 mm. wide hydrophobic zone between the second and third reaction zones. Since, in this manner, only gaseous ammonia passes over to the third reaction zone, other bases and acids present do not disturb the reaction. Furthermore, by means of buffering, the first test zone can be adjusted to an optimum pH value for urease so long as the degree of alkalinity of the second test zone is sufficient to liberate the ammonia quantitatively.

In spite of results which are of good diagnostic value, these test strips suffer from a number of disadvantages. The determination can only be carried out with serum or plasma but not with blood because the blood corpuscles disturb the chromatography. This necessitates centrifuging the blood, i.e., a large sample is needed and can only be obtained by a physician or appropriately well-trained personnel. In order to make the transmission of the ammonia through the gas space reproducible, the test strips must, in addition, be suspended in a special reaction chamber and precisely fixed relative to the sample during the reaction period. For the chromatography in the first and second reaction zones and especially for the diffusion of the ammonia through the gas space, a reaction time of 30 minutes is necessary, so that the test strips can scarcely be called rapid tests.

In German Pat. No. 2,249,647, there is described a similarly constructed test strip which possesses some constructional improvements. In this case, determinations can also be carried out on whole blood. However, in normal cases, these test strips also require a reaction time of 30 minutes and also require the use of a reaction chamber.

A further disadvantage of both of the above-mentioned test strips is the fact that the concentration of the urea takes place with a visual longitudinal measurement of the colorchanging zone of the indicator paper with an unclear boundary zone which is difficult to assess and cannot be carried out by the visual or precise measurement of the color depth with a remission photometer.

In German Pat. No. 2,626,367, there is described a device with several layers lying one on top of the other. For the detection of urea, these consist of a urease-containing layer, an alkaline buffer-containing layer and an indicator layer for detecting gaseous ammonia. In order to prevent the undesired diffusion of sample fluid from the urease layer to the indicator zone in addition to the gaseous ammonia, the urease layer and the indicator layer lying thereunder are separated by a hydrophobic, gas-permeable film or the indicator layer is made in the form of a hydrophobic film. The indicator layer, the intensity of the color of which differs according to the urea content of the sample, is measured through a carrier film and the concentration of the urea is thus determined.

In order to achieve reaction times of about 10 minutes, this test device must be incubated at 40°–50° C. because of the relatively high impermeability of the separating layer. Because of the cost of apparatus which this involves, it is not possible to use this test device as a rapid test.

Thus, all the previously known test strips for the determination of urea suffer from substantial disadvantages.

The present invention provides a device for the detection of urea in body fluids which: is simple to handle and does not require the additional use of a reaction chamber; enable a urea determination to be carried out not only in serum or plasma but also in small amounts of whole blood; at ambient temperature requires a reaction time of at most 10 minutes and preferably of about 5 minutes; gives semiquantitative results in the case of visual assessment; and in the case of remission photometric evaluation, enables a quantitative determination of urea to be carried out.

SUMMARY

According to the present invention, there is provided a diagnostic device for the determination of ammonia and of substrates reacting with the formation of ammonia, comprising a handle, an indicator layer for gaseous ammonia fixed thereon and an alkaline buffer-containing reaction layer which optionally contains additional reagents reacting with the substrate with the formation of ammonia, wherein the indicator layer is securely attached to the handle and above it is arranged the reaction layer at a distance of 10 to 200μ by means of a distance piece, the distance piece and the reaction layer being easily removable from the indicator layer.

DESCRIPTION OF THE DRAWING

The present invention will be more fully understood from the following description taken in conjunction with the accompanying drawing which is an exploded side view of a device according to the invention.

DESCRIPTION

The device of the invention can be used not only for the detection and quantitative determination of ammonia itself but also of ammonium salts and of substrates which react with the liberation of ammonia when, instead of urease, there are used the appropriate reagents which react with the substrate in question with the formation of ammonia. The following substrate/reagent combinations are mentioned by way of example:
  urea/urease;
  creatinine/creatinine deiminase;
  amino acid/amino acid dehydrogenase;
  amino acid/amino acid oxidase;
  amino acid/amino acid dehydratase;
  amino acid/ammonia lyase;
  amine/amine oxidase;
  diamine/amine oxidase;
  glucose/phosphoramidate-hexose-phosphoric transferase and phosphoramidate;
  adenosine diphosphate/carbamate kinase and carbamoyl phosphate;
  acid amide/amidohydrolase;
  nucleobase/deaminase;
  nucleoside/deaminase; and
  nucleotide/deaminase.

The present invention is characterized by an ammonia-forming and simultaneously ammonia-expelling reaction layer fixed at a small but exactly reproducible distance above an indicator layer without the free diffusion of the ammonia through films, layers and the like being hindered. Free diffusion and a small distance are prerequisites for a short reaction time. Only with an exactly reproducible distance of both layers, even in the case of large scale production, can such a test strip satisfy the quantitative requirements.

One embodiment of the device of the invention is shown in the drawing. The device includes an indicator layer 1 which preferably consists of an absorbent carrier, such as paper, a porous synthetic resin or the like, and contains a reagent mixture, the remission photometric properties of which are changed gradually by the action of gaseous ammonia, depending upon the amount of ammonia. The indicator layer preferably contains an appropriate pH indicator, which is preferably a tetranitrodiphenylmethylpyridine indicator (as described in commonly-owned copending application Ser. No. 34,720 filed Apr. 30, 1979) and a buffer, for example a citrate, tartrate or malonate buffer or also a polymeric buffer, for example a polyacrylate or polymethacrylate or copolymer thereof or some other carboxyl group-containing polymer.

Over the indicator layer 1 there is arranged a spacer 2 which has a constant thickness of about 10 to 200μ and also a uniform hold surface, the open area of which accounts for at least 25% of the total surface area. The spacer can consist of a hydrophobed woven or knitted mesh or of a perforated film which satisfies the above requirements, it being preferable to employ a hydrophobed woven fabric. Such meshes are known, for example, as screen printing cloth or as bolting cloth.

In the case of a perforated film, there can be used a film with many relatively small holes which then corresponds practically to a woven mesh but a film can also be used which only has one large hole exactly over the middle of the test region.

Above the spacer 2, there is a reaction layer 3 which preferably consists of an absorbent carrier, for example paper. This reaction layer 3 contains the ammonia-forming reagents, an alkaline buffer, for example an ethylenediaminetetraacetate (EDTA), tris-(hydroxymethyl)-aminomethane (TRIS) or a phosphate buffer, with a pH of 7 to 9.5, a TRIS buffer with a pH of 8.5 being preferred, and adjuvants, such as wetting agents and/or stabilizers.

The reaction layer 3 is preferably held firmly with a mesh 4, for example a woven or knitted material or the like, in the manner described in German Pat. No. 2,118,455 but it can also be securely stuck or sealed onto the distance piece in some other manner. As shown in the drawing, one end of the spacer 2 extends beyond layer 3 and mesh 4 so that all three members can be readily stripped off or removed together at the end of a test to reveal indicator lever 1.

For carrying out a substrate determination, a drop of test fluid is applied to the reaction layer 3. In order to prevent the upward escape of ammonia, the upper side of the reaction layer is preferably covered with an appropriate layer, for example with an adhesive label or the like. After a reaction time of 2 to 10 minutes and normally of 5 to 7 minutes, the reaction layer and the spacer are pulled off. The coloration of the thus uncovered indicator layer can be measured quantitatively with a remission photometer or semiquantitatively by visual comparison with standard colors.

The following examples are intended to illustrate the present invention:

EXAMPLE 1

Quantitative Determination of Urea in Serum (a) Urease paper (3)

Filter paper is impregnated with a solution with the following composition, dried and then cut up into 6 mm. wide strips:

| | |
|---|---|
| urease (5U/g.) | 6 g. |
| dithioerythritol | 0.1 g. |
| 0.3M TRIS . HCl buffer (pH 8.5) | 100 ml. |

(b) Indicator

Filter paper is impregnated with a solution with the following composition, dried and also cut up into strips with a width of 6 mm.

| | |
|---|---|
| N-[bis-(2,4-dinitrophenyl)-methyl]-4-tert.-butyl-pyridinium chloride | 0.39 g. |
| ethylene glycol monomethyl ether | 42 ml. |
| 0.25 M sodium malonate buffer (pH 2.8) | 48 ml. |

(c) Spacer (2)

Screen printing cloth with a filament thickness of about 100μ and with an open surface area of about 35% of the whole surface area is rendered hydrophobic with silicone resin and cut up into 25 to 40 mm. wide strips.

(d) Covering mesh (4)

Hydrophilic nylon mesh of about 60μ thickness and 40μ filament thickness and with a free holed surface area of about 65% of the whole surface area is cut up into 15 mm. wide bands.

(e) Handle (5)

As carrier film and handle, there is used a 6 to 10 cm. wide, approximately 0.2 to 0.3 mm. thick band of melt adhesive-coated polyester film.

Production of the test strips

Urease paper (3), indicator paper (1) and spacer (2) are sealed together with a mesh (4) covering the urease paper, as shown in the drawing, onto the end of the 6 to 10 cm. wide handle (5) coated with melt adhesive and the resultant band is cut up into 6 mm. wide strips so that 6×6 mm. test zones result on a 6 to 10 cm. long handle.

10 μl. of serum is dropped onto the covering mesh of such a strip and covered with an adhesive label. After a reaction time of 7 minutes, the urease paper (3) and covering mesh (4) are removed, together with the spacer (2). The coloration of the indicator layer (1) is measured from above with a remission photometer. Depending upon the urea concentration, the following measurement values are obtained:

| mg. urea/100 ml. serum | measurement signal (scale divisions) ± 1 s; average value from 10 values |
|---|---|
| 20 | 12.9 ± 0.75 |
| 40 | 27.5 ± 1.5 |
| 60 | 46.1 ± 1.9 |
| 80 | 61.5 ± 1.4 |
| 100 | 69.0 ± 0.4 |
| 150 | 77.2 ± 0.5 |
| 200 | 79.4 ± 0.5 |

EXAMPLE 2

Quantitative Detection of Urea in Blood (a) Urease paper (3)

Same as Example 1.

(b) Indicator paper (1)

Filter paper is impregnated with a solution of the following composition and dried:

| | |
|---|---|
| N-[bis-(2,4-dinitrophenyl)-methyl]-4-tert.-butyl-pyridinium chloride | 0.44 g. |
| ethylene glycol monomethyl ether | 40 ml. |
| polyacrylate ("Acrytex" SL 865 of the firm Rohm) | 6 g. |
| water | 60 ml. |
| ("Acrytex" is a Registered Trade Mark). | |

(c) Spacer (2)

20μ thick polypropylene film with a perforated surface of 35 to 45% of the whole surface area.

(d) Covering mesh (4)

Same as Example 1.

(e) Handle (5)

Same as Example 1.

The production of the test strips and the urea determination are carried out as described in Example 1 but with the use of EDTA blood plasma, the following results being obtained:

| mg. urea/100 m. plasma | measurement signals (scale divisions) ± 1 s; average values from 10 values |
|---|---|
| 20 | 11.6 ± 0.6 |
| 40 | 23.0 ± 1.3 |
| 60 | 41.2 ± 1.9 |
| 80 | 56.7 ± 1.5 |
| 100 | 66.4 ± 0.5 |
| 150 | 75.3 ± 0.5 |
| 200 | 78.2 ± 0.4 |

EXAMPLE 3

Semiquantitative Detection of Urea in Blood (a) Urease paper (3)

Same as Example 1.

(b) Indicator paper (1)

Filter paper is impregnated with a solution of the following composition and dried at 70° C.:

| | |
|---|---|
| bromophenol blue | 0.1 g. |
| ethylene glycol monomethyl ether | 9 ml. |
| tartaric acid | 0.4 g. |
| water | 21 m. |

(c) Spacer (2)

Polyamide fleece with a thickness of about 80μ and hydrophobed with silicone resin.

(d) Covering mesh (4) and Handles (5)

Same as Example 1.

Preparation is the same as Example 1.

For urea determination in whole blood, a drop of blood is applied to the test strip. After a reaction time of 7 minutes, reaction colors which can be visually easily differentiated are obtained according to the urea content:

| mg. urea/100 ml. blood | color |
| --- | --- |
| 20 | yellow |
| 40 | greenish-yellow |
| 60 | yellow-green |
| 80 | green |
| 100 | blue-green |
| 150 | greenish-blue |
| 200 | blue |

EXAMPLE 4

Quantitative Detection of Creatinine in Serum or Blood (a) Creatinine deiminase paper Filter paper is impregnated with a solution of the following composition, dried and cut up into 6 mm. wide bands:

| creatinine deiminase | 2000 U |
| --- | --- |
| dithioerythritol | 0.1 g. |
| 0.3M TRIS . HCl buffer (pH 8.5) | 100 ml. |

(b) Indicator layer

A mass of the following composition is coated with a thickness of 0.1 mm. onto a polycarbonate film, dried and cut up into 6 mm. bands:

| N-[bis-(2,4-dinitrophenyl)-methyl]-4-tert.-butyl-pyridinium chloride | 0.14 g. |
| --- | --- |
| hydroxypropylcellulose ("Culminal" PK 82 (Henkel)) | 0.18 g. |
| water | 30 ml. |
| 0.01N hydrochloric acid | 1.5 ml. |
| ("Culminal" is a Registered Trade Mark). | |

(c) Spacer

Screen printing cloth of about 100μ filament thickness and with an open surface area of about 35% of the whole surface area is hydrophobed with silicone resin and cut up into 25 to 40 mm. wide bands.

(d) Covering mesh

Hydrophilic nylon mesh of about 60μ thickness and 40μ filament strength and with approximately 65% free hole surface area of the whole surface area is cut up into 15 mm. wide bands.

(e) Handle

As carrier foil and handle, there is used a 6 to 10 cm. wide and approximately 0.2 to 0.3 mm. thick band of melt adhesive-coated polyester film.

Production of the test strips

Creatinine deiminase paper (3), indicator paper (1) and spacer (2) are sealed, together with a mesh (4) covering the creatinine deiminase paper as shown in the FIGURE of the accompanying drawing, onto the end of the 6 to 10 cm. wide film coated with melt adhesive and the resultant band is cut up into 6 to 10 mm. wide strips, so that 6×6 mm. test zones result on a 6 to 10 cm. long handle.

10 μl. of serum are applied to the covering mesh of such a strip and closed with an adhesive label. After a reaction time of 7 minutes, the creatinine deiminase paper and the covering mesh are removed, together with the spacer. The coloration of the indicator layer is measured from above with a remission photometer. Depending upon the creatinine concentration, the following measurement values are obtained:

| mg. creatinine/ 100 ml. | measurement signal (scale divisions) |
| --- | --- |
| 0 | 28 |
| 0.5 | 37 |
| 1 | 47 |
| 2 | 60 |
| 3 | 68 |
| 4 | 73 |
| 5 | 76 |
| 6 | 78 |
| 7 | 80 |
| 8 | 82 |
| 9 | 83 |
| 10 | 84 |

The creatinine concentrations determined in this manner are, of course, still falsified by the ammonia which is also present in the serum. The true creatinine values are obtained when the ammonia concentration values obtained according to the following Example 5 are substracted or the ammonia is removed from the serum before the measurement by suitable means, for example with an ion exchanger.

The falsification due to ammonia is only of importance in the case of creatinine determinations but not in the case of the urea determination according to Examples 1 and 2 because of the more favorable ratios of the normal values occurring in the serum:

| ammonia | 0.016–0.038 mMol/l. |
| --- | --- |
| creatinine | 0.044–0.097 mMol/l. |
| urea | 3.5–8.3 mMol/l. |

EXAMPLE 5

Quantitative Determination of Ammonia in Serum or Blood (a) Ammonia-expelling paper Filter paper is impregnated with an aqueous solution of 0.3 M TRIS.HCl buffer (pH 9), dried and cut up into 6 mm. side bands.

(b)–(e) Analogous to Example 4

The production and use of the test strips is also analogous to Example 4.

Depending upon the ammonia concentrations, the following measurement values are obtained:

| μg. ammonia/ 100 ml. | measurement signal (scale divisions) |
| --- | --- |
| 0 | 27 |
| 50 | 41 |
| 100 | 50 |
| 150 | 54 |
| 200 | 59 |
| 300 | 65 |
| 600 | 75 |
| 1500 | 85 |

What is claimed is:

1. Diagnostic device for the determination of ammonia and of substrates reacting with the formation of ammonia, comprising handle means, and indicator layer for gaseous ammonia on said handle means, an alkaline buffercontainer reaction layer, said reaction layer being positioned a distance of 10 to 200μ above the indicator layer by spacer means, said spacer means and the reaction layer being readily separable from the indicator layer.

2. Device of claim 1 wherein the spacer means is a woven or knitted mesh or a perforated film with a thickness of 10 to 200μ and a free open surface area of at least 25% of the total surface area.

3. Device of claim 1 wherein the handle means is made of a synthetic resin.

4. Device of claim 1 wherein the reaction layer contains a wetting agent and/or stabilizer.

5. Device of claim 1 wherein the reaction layer is secured to the handle by a hydrophilic, fluid-permeable covering layer.

6. Device of claim 5 wherein said covering layer is a woven or knitted fabric.

7. Device of claim 1, wherein the reaction layer contains additional reagents reacting with the substrate to form ammonia.

8. Device of claim 7 wherein the reaction layer contains urease.

9. Device of claim 7 wherein the reaction layer contains creatinine deiminase.

10. Process for detecting ammonia and of substrates reacting with the formation of ammonia in aqueous solution which comprises impregnating the reaction layer of a device according to claim 1 with a drop ammonia or of a substrate reacting with the formation of ammonia thereby causing ammonia to be liberated and act on the indicator layer, stripping off the reaction layer and the spacer means and determining the coloration of the indicator layer visually or photometrically.

11. Process of claim 10 wherein the reaction layer contains urease which is impregnated with a drop of urea-containing solution.

12. Process of claim 10 wherein the reaction layer contains creatinine deiminase which is impregnated with a drop of creatinine-containing solution.

13. Process of claim 10 wherein the reaction layer is covered during the reaction.

* * * * *